United States Patent [19]

Moss

[11] Patent Number: 5,139,486
[45] Date of Patent: Aug. 18, 1992

[54] DILATOR/INTRODUCER FOR PERCUTANEOUS GASTROSTOMY

[76] Inventor: Gerald Moss, RD #1, West Sand Lake, N.Y. 12196

[21] Appl. No.: 636,665

[22] Filed: Jan. 2, 1991

[51] Int. Cl.⁵ .......................................... A61M 25/01
[52] U.S. Cl. ................................... 604/164; 604/158; 604/264
[58] Field of Search .............. 604/158, 164, 165, 264; 606/191, 194, 195; 128/785, 786

[56] References Cited

U.S. PATENT DOCUMENTS

| | | | |
|---|---|---|---|
| 3,993,079 | 11/1976 | Henriques de Gatztañov ... | 604/164 |
| 4,581,019 | 4/1986 | Curelaru et al. .................... | 604/164 |
| 4,585,013 | 4/1986 | Harris ................................... | 128/786 |
| 4,588,398 | 5/1986 | Daugherty et al. ................. | 604/164 |
| 4,629,450 | 12/1986 | Suzuki et al. ........................ | 604/164 |
| 4,850,960 | 7/1989 | Gravzel ................................. | 604/158 |
| 4,861,334 | 8/1989 | Nawaz ................................... | 604/164 |
| 4,895,564 | 1/1990 | Farrell ................................... | 604/164 |
| 5,057,083 | 10/1991 | Gellman ............................... | 604/164 |

*Primary Examiner*—C. Fred Rosenbaum
*Assistant Examiner*—William W. Lewis
*Attorney, Agent, or Firm*—Schmeiser, Morelle & Watts

[57] ABSTRACT

An improved dilator/introducer used to facilitate the placement of a catheter within an internal area of a body. The introducer portion of the device has a tapered and bevelled forward end. The dilator portion of the device has a longitudinally extending slot located proximate its rearward end to provide a side exit point for a "J"-wire. Optionally, a plug also having a slot can be received within the rearward end of the dilator to provide an enlarged, smooth surface area that can receive pressure from the palm area of the inserter's hand.

10 Claims, 2 Drawing Sheets

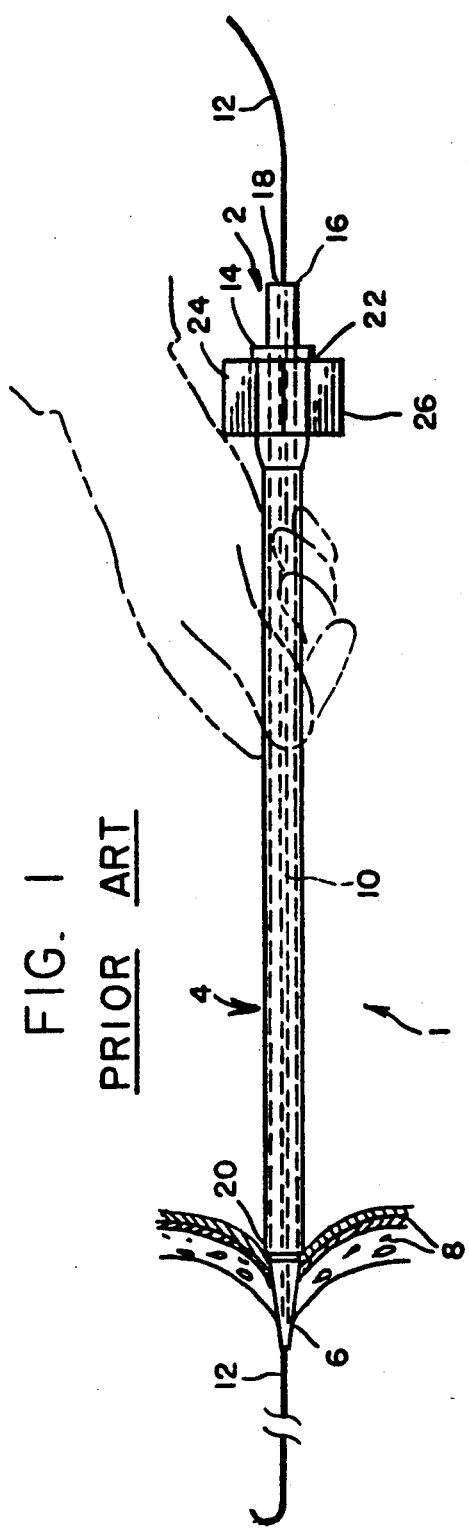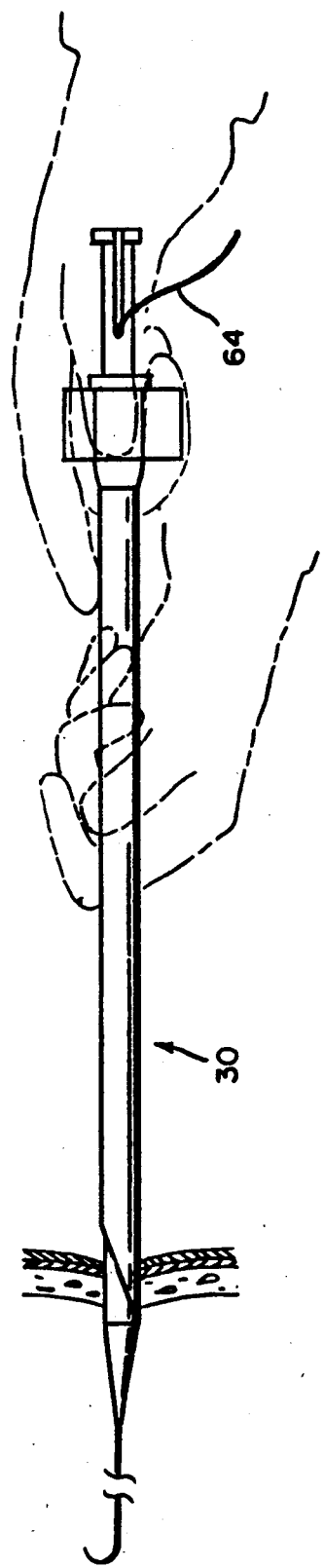

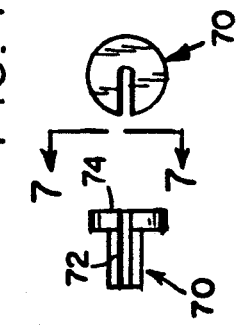
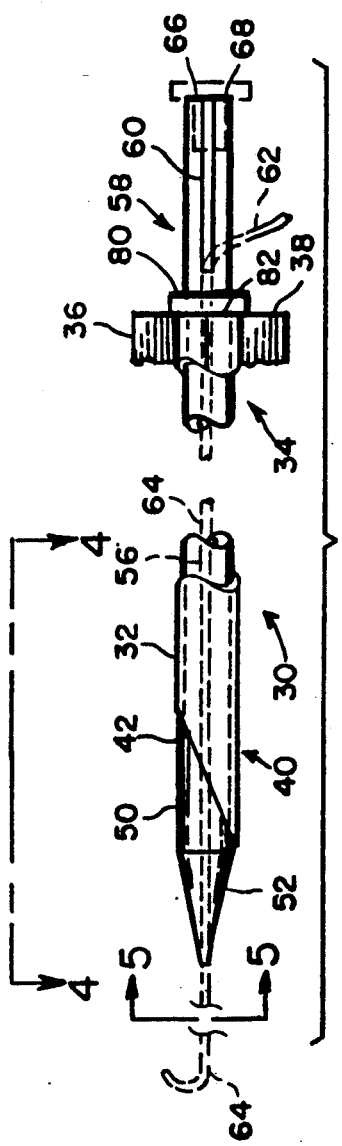
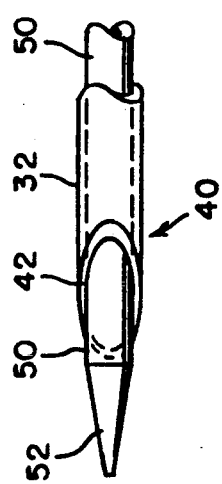
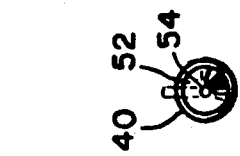

DILATOR/INTRODUCER FOR PERCUTANEOUS GASTROSTOMY

FIELD OF THE INVENTION

The invention is in the field of medical devices. More specifically, the invention is an improved dilator/introducer that is used to facilitate the placement of a catheter within a body. The invention can be used in a number of surgical procedures and is ideal for use in a percutaneous gastrostomy.

BACKGROUND OF THE INVENTION

A percutaneous gastrostomy involves the placement of a catheter within the stomach area of a living body. The latest procedures for performing a gastrostomy involve an initial percutaneous securement of the stomach to the abdominal wall. Once the stomach is fixed in place, a hollow needle is inserted through the skin and into the stomach area. Next, a "J" wire is introduced percutaneously into the stomach via the interior of the hollow needle. At this point, the "J" wire may be further positioned by use of a gastroscope and biopsy forceps. A hollow dilator/introducer is then inserted into the body with the "J" wire passing through its center.

A dilator/introducer is a multiple-piece device that comprises a pointed dilator needle partially housed within a close fitting elongated introducer tube. The front and rear ends of the introducer tube are flat with the plane of the openings being perpendicular to the longitudinal axis of the tube. When the introducer is mounted on the dilator, the front end of the introducer is located proximate the rear portion of the dilator's tapered point.

The dilator functions to gently spread the tissue away from the entry hole originally made in the body and thereby to allow the relatively large diameter introducer to pass through the hole with a minimum of resultant tissue trauma or damage. Once the introducer is properly positioned, the dilator is removed from the body and slid off the portion of the "J" wire that is exterior to the body. Next, a catheter is slid onto the exterior portion of the "J" wire and pushed into the body via the center passage of the hollow introducer tube. Once the catheter is in place, the introducer is gently pulled from the body. To remove the introducer from the catheter, the introducer is adapted to longitudinally split in half once pressure is applied to a pair of ear portions located at the rear of the introducer.

There are three problems that are experienced when using a conventional dilator/introducer apparatus.

The first problem is a tearing or traumatizing of the tissue during the insertion process. After the dilator initially spreads the tissue, portions of the tissue contact small gaps located between the front end of the introducer and the dilator. Depending on the size and shape of the gaps, the tissue can become trapped or torn. These gaps occur when the round shape of the forward end of the introducer does not contact the dilator for the full 360 degrees of the introducer's opening due to an improper or inexact machining of the two parts that make up the dilator/introducer. The machining problems are most noticeable with large bore introducers or cannulas that are sized to inwardly receive a large diameter stomach tube.

The second problem found with prior art dilator/introducers is that the front tip of the introducer acts as a stop during the insertion process. When dealing with large bore introducers, (for example, to receive a 6 mm. stomach tube) the wall thickness of the introducer must be great enough to prevent its being bent or broken during the surgical procedure. The shape of the introducer's opening in conjunction with its relatively large wall thickness requires the tissue to expand abruptly about the entire circumference of the introducer's tip when the introducer first contacts the tissue. The tip of the introducer effectively acts as a thick circular ridge about the dilator, which stops the smooth entry of the device into the body.

The third problem with a conventional dilator/introducer apparatus is that the physician must grasp the device in an awkward manner during the insertion process. A secure and comfortable grip is prevented by the "J"-wire's exiting from the flat rear face of the dilator portion. The physician cannot apply force directly against the rear end of the dilator portion lest a crimping of the "J" wire should result. Therefore, the device must be gripped only along its sides. This leads to a less secure grip on the device in which slippage may occur. Also, gripping the device between its ends is somewhat awkward and this reduces the effectiveness and control of the physician's pushing action when the device is inserted into the body.

SUMMARY OF THE INVENTION

The invention is an improved dilator/introducer apparatus in which both the dilator and the introducer are pointed. It is designed to overcome the problems associated with the dilator and introducer portions of prior art dilator/introducers. The invention is used to place a catheter or similar tube within a body during a percutaneous gastrostomy or other surgical procedure.

The forward end of the introducer portion of the invention is modified to significantly reduce tissue damage during the insertion process. To achieve this result, the forward end of the introducer is tapered in the fashion of a needle but with the leading tip beveled toward the lumen to thereby present a gradual increasing of diameter as the introducer passes through the tissue layer(s). This also allows the tissue to press the end of the introducer against the dilator and thereby to some extent negate any dimensional differences between the inner diameter of the introducer portion and the outer diameter of the dilator portion.

The rearward end of the dilator portion has been modified in order to facilitate grasping of the device. A longitudinal slot is located in the dilator portion proximate its rearward end to allow the "J" wire to exit from the side of the dilator portion. This allows the physician to apply direct pressure against the rear face of the dilator portion thereby greatly improving the directional stability and force transfer during the insertion process. Since the rearward end of the dilator portion can be fitted into the physician's palm, the chance of slippage is greatly reduced.

Also disclosed is an optional plug that can be used to close off the rearward open end of the slotted dilator portion. The plug is preferably larger in outer diameter than the dilator portion and provides an increased surface are for the physician to push against during the insertion process. The plug may also include a longitudinal slot to provide the physician with the option of having the "J" wire exit either from the side or the rear face of the dilator portion.

The invention can be manufactured in appropriate sizes to facilitate the insertion of small or large diameter tubes within a body. Unlike the prior art devices of this type, even 6 mm. diameter tubes can be easily placed within a body.

BRIEF DESCRIPTION OF THE DRAWINGS

FIG. 1 shows a prior art dilator/introducer being inserted through an outer layer of body tissue.

FIG. 2 shows a dilator/introducer in accordance with the invention being inserted through an outer layer of body tissue.

FIG. 3 is a side view of the dilator/introducer shown in FIG. 2. An end cap is shown in phantom.

FIG. 4 is a top view of the forward portion of the dilator/introducer shown in FIG. 3.

FIG. 5 is an end view of the forward portion of the dilator/introducer shown in FIG. 3.

FIG. 6 is a side view of a rear plug.

FIG. 7 is an end view of the rear plug shown in FIG. 6.

DETAILED DESCRIPTION OF THE DRAWINGS

Referring now to the drawings in greater detail, wherein like reference characters refer to like parts throughout the several FIGURES, there is shown by the numeral 1 a prior art dilator/introducer.

The prior art dilator/introducer is composed of two separate parts. A hollow dilator portion 2 is removably housed within a cannula-like introducer portion 4. The dilator has a tapered needle-like tip 6 that functions to gradually spread apart the tissue as the device is pushed through the tissue layers 8. This can be seen in FIG. 1 where the tissue has been spread open or dilated by the tip 6. Within the dilator portion is a continuous thru-passage 10. A flexible "J"-wire 12 is shown within the passage.

The rearward part of the dilator portion includes a circumferential ridge 14 that limits the forward travel of the dilator portion within the introducer portion 4. The dilator portion has a flat rear face 16 that includes an exit orifice 18 through which a portion of the "J"-wire 12 extends.

The introducer portion 4 is tubular in shape and has flat front and rear ends 20 and 22, respectively. The front end of the introducer portion is shown positioned at a point slightly behind the tapered tip 6 of the dilator portion. As shown in FIG. 1, the flat front end 20 of the introducer portion does not have a shape that functions to expand the tissue as the device is pushed forward into a body. This causes the tissue to catch on the end 20 and be pulled inwardly. In addition, unless the device has been manufactured to exact dimensions, an air gap (not shown) may be present between the interior wall of the introducer portion and the forward exterior surface of the dilator portion. This gap can cause a coring of the tissue or lead to excessive tissue trauma.

Typically, the introducer portion 4 will be of the breakaway type in which two rear ears 24 and 26 are fastened to the rear of the tube. By applying simultaneous outward radial pressure on the two ears, the introducer is caused to split in half along its longitudinal axis. To facilitate splitting of the introducer, a narrow longitudinal internal groove will normally have been made in the introducer tube during its manufacture. The rear end 22 of the introducer portion is flat and sized to allow a firm contact between itself and the dilator ridge 14.

FIGS. 2-7 show a dilator/introducer 30 in accordance with the invention. FIG. 2 shows the device being inserted into a body.

FIG. 3 shows a side view of the dilator/introducer device shown in FIG. 2. As found in the prior art, the dilator/introducer is made up from two separable main parts, namely an introducer 32 and a dilator 50.

The tube-like introducer 32 is of the breakaway type in which the structure of the introducer is adapted to facilitate a longitudinal splitting in half of the device. The rear portion 34 of the introducer is basically identical to that of the prior art and includes a pair of ears 36 and 38 attached to rear portions of the introducer tube.

The forward end 40 of the introducer is unlike the prior art since it includes a tapered, needle-like open tip 42 through which the front end of the dilator 50 passes. The angled opening 42 can be seen in FIGS. 2, 3 and 4. The opening is sized to closely fit the exterior of the dilator. By tapering the tip 42, a number of advantages are provided over the straight flat tip employed by the prior art.

The tapered tip reduces the chances of tissue trauma or tearing when the dilator/introducer is first inserted through the tissue. The gradually increasing outer diameter produces a dilating effect on the tissue similar to that realized by the tapered, needle-like tip of the dilator. As the tip of the introducer first encounters the tissue, it pushes the tissue outwardly. At the same time, the tissue exerts an opposite force on the introducer and pushes the tip of the introducer inwardly against the dilator. This tends to eliminate any gaps that may exist between the inner wall of the introducer and exterior of the dilator. As a result, the device is less damaging to the tissue. Additionally, the elimination of any air gaps reduces the chances of contaminants reaching the tissue.

The hollow dilator 50 has a front tip 52 that is similar to the dilator portions of the prior art. The tip is tapered and has a center orifice 54 that leads to a longitudinally extending passage 56 that extends the length of the dilator.

The rearward portion 58 of the dilator differs considerably from the prior art. A longitudinally extending slot 60 is present in the wall of the dilator and forms a side opening into the interior passage 56. This allows the end 62 of the "J"-wire 64 to extend from the side of the dilator instead of exiting directly from the dilator's rear opening 66.

The use of a rear slot greatly facilitates the insertion of the dilator/introducer through the tissue layers. When the "J"-wire exits the dilator through the slot, the physician is able to apply pressure directly against the rear face 68 of the dilator without worrying about bending or crimping the delicate "J"-wire.

A stopper member such as a plug 70 may optionally be inserted into the rear opening 66 of the dilator. The plug serves to provide a larger surface area for the doctor's hand to bear on during the insertion procedure. The plug is shown as having a longitudinal slot 22 that extends the length of the plug. The slot provides the physician with the option of allowing the "J"-wire to exit from the dilator slot or to be pulled rearwardly and exit directly from the rear face 74 of the plug. If the plug is rotated so that its slot 72 does not align with the dilator slot 60, the plug then functions to fix the exit point of the "J" wire (i.e.—if the wire is located in slot 60, the plug can be rotated or placed so that it prevents the wire from moving to the rearward, blocked portion of the slot).

It should be noted that other types of stopper members can be attached to the rearward end of the dilator in lieu of a plug. For example, a cap having an internal diameter slightly greater than the external diameter of the dilator can be attached to the rearward end of the dilator and serve the same purpose (i.e. to abut the hand).

The advantages of the instant invention are most evident in a brief description of the invention's use.

In an intermediate stage of a gastrostomy, one end of the "J"-wire extends out of the body from a small hole in the area of the stomach. The front bent portion of the wire is located in the stomach area and the physician is ready to place a catheter into the stomach area.

The dilator/introducer is then readied by inserting the dilator within the introducer until the dilator ridge 80 contacts the rear face 82 of the introducer. When the dilator/introducer is fully assembled, the tip 52 of the dilator extends just past the tapered opening 42 of the introducer. Next, the portion of the "J"-wire extending outwardly from the body is threaded through the dilator until the wire's outer end exists from the dilator's rear opening 66. The dilator/introducer is then moved on the wire until the tip of the dilator is proximate the hole in the body tissue.

The physician then moves the end of the "J"-wire so that it exits from the dilator slot 60. At this point, the doctor can, if desired, place plug 70 into the rear portion of the dilator. The doctor then holds the dilator/introducer in the manner shown in FIG. 2 and applies pressure directly against the rearward end of the dilator or, if the plug is used, the rear face 74 of the plug. Being able to apply pressure in this manner allows greater directional stability and a firmer contact than was available to a user of the prior art dilator/introducer shown in FIG. 1.

Once the dilator/introducer 30 is properly positioned, the physician carefully inserts its forward portion through the entry hole in the tissue. The tapered leading ends of the dilator and the introducer gently enlarge the hole as the device is inserted. The physician continues to insert the dilator/introducer into the body until the tip of the introducer portion is in the desired position within the organ cavity or other area.

The dilator portion 50 of the dilator/introducer is then pulled rearwardly while the introducer portion 32 and "J"-wire 64 are held in position. The dilator portion is disposed of after it is removed from the portion of the "J"-wire exterior to the body.

The catheter is then placed within the body by threading it along the "J"-wire with the "J"-wire passing through the interior passage of the catheter. The catheter passes through the now empty interior passage of the introducer and thereby is easily routed to its proper position within the body. Once the catheter is in place, the introducer portion is eased out of the body. To remove the introducer 32 from the catheter, appropriate outward pressure is applied to the introducer ears 36 and 38. This causes a longitudinal splitting of the introducer and it falls away from the catheter.

The embodiments of the invention disclosed herein have been discussed for the purpose of familiarizing the reader with the novel aspects of the invention. Although a preferred embodiment of the invention has been shown and described, many changes, modifications and substitutions may be made by one having ordinary skill in the art without necessarily departing from the spirit and scope of the invention.

I claim:

1. A dilator/introducer for facilitating the placement of a catheter within a body, said dilator/introducer comprising:
    a needle shaped introducer having a forward end, a rearward end, a throughbore extending between said forward and rearward ends and wherein said forward end is tapered; and
    a needle shaped dilator sized to be received within said introducer and having a forward tapered end, a rearward end, an exterior surface, a throughbore extending between said forward and rearward ends and a longitudinally extending slot means located proximate said rearward end and extending between said exterior surface and a rear portion of said dilator throughbore wherein when a wire is located within said dilator throughbore, a portion of said wire can exit from said throughbore via said slot means.

2. The dilator/introducer of claim 1 further comprising a stopper member attached to the rearward end of the dilator.

3. The dilator/introducer of claim 2 wherein the stopper member is a plug that has a forward end of a first diameter and a rearward end of a second diameter and wherein said first diameter is substantially equal to an interior diameter of the dilator throughbore.

4. The dilator/introducer of claim 3 wherein the diameter of the rearward end of said plug is at least equal to the diameter of the rearward end of said dilator.

5. The dilator/introducer of claim 2 wherein said stopper member comprises a longitudinal slot that extends the length of said member wherein said slot of said member can be aligned with the dilator slot means and thereby allow a wire exiting from said dilator slot means to be moved rearwardly and exit from a rear face of said stopper member.

6. A dilator/introducer for facilitating the placement of a catheter within a body, said dilator/introducer comprising:
    a tubular introducer having a forward end, a rearward end, and a throughbore extending between said forward and rearward ends; and
    a needle shaped dilator sized to be received within said introducer and having a forward tapered end, a rearward end, an exterior surface, a throughbore extending between said forward and rearward ends and a longitudinally extending slot located proximate said rearward end and extending between said exterior surface and a rear portion of said dilator throughbore wherein when a wire is located within said dilator throughbore, a portion of said wire can exit from said throughbore via said slot.

7. The dilator/introducer of claim 6 further comprising a stopper member attached to a rear portion of said dilator.

8. The dilator/introducer of claim 7 wherein the stopper member is a plug that has a forward end of a first diameter and a rearward end of a second diameter wherein said first diameter is substantially equal to an interior diameter of the dilator throughbore.

9. The plug of claim 8 wherein the diameter of the rearward end of said plug is at least equal to the diameter of the rearward end of said dilator.

10. The dilator/introducer of claim 7 wherein said stopper member further comprises a longitudinal slot that extends the length of said member wherein said member slot can be aligned with the dilator slot and thereby allow a wire exiting from said dilator slot to be moved rearwardly and exit from a rear face of said stopper member.

* * * * *